(12) United States Patent
Hall et al.

(10) Patent No.: US 6,777,238 B1
(45) Date of Patent: Aug. 17, 2004

(54) DUAL USE CORROSION INHIBITOR AND PENETRANT FOR ANOMALY DETECTION IN NEUTRON/X RADIOGRAPHY

(75) Inventors: Phillip B. Hall, Huntsville, AL (US); Howard L. Novak, Indialantic, FL (US)

(73) Assignee: The United States of America as represented by the Administrator of the National Aeronautics and Space Administration, Washington, DC (US)

(*) Notice: Subject to any disclaimer, the term of this patent is extended or adjusted under 35 U.S.C. 154(b) by 113 days.

(21) Appl. No.: 10/011,228

(22) Filed: Nov. 27, 2001

(51) Int. Cl.[7] .............................................. G01N 31/00
(52) U.S. Cl. ................... 436/6; 436/5; 436/8; 252/387; 422/7
(58) Field of Search ............................. 436/2, 5, 6, 8; 252/387; 422/7

(56) References Cited

U.S. PATENT DOCUMENTS

| | | | | |
|---|---|---|---|---|
| 3,652,224 A | * | 3/1972 | Johnson et al. ................. 436/5 |
| 4,172,224 A | * | 10/1979 | Lapinski et al. ............. 250/302 |
| 4,457,174 A | * | 7/1984 | Bar-Cohen et al. ........... 73/598 |
| 4,587,555 A | * | 5/1986 | Carollo et al. ............. 378/98.5 |
| 4,877,638 A | * | 10/1989 | Novak et al. .................. 427/8 |
| 6,068,711 A | * | 5/2000 | Lu et al. ..................... 148/273 |
| 6,076,405 A | * | 6/2000 | Schoess ....................... 73/587 |
| 6,148,061 A | * | 11/2000 | Shefer et al. ............... 378/121 |
| 2001/0006215 A1 | * | 7/2001 | Cowan et al. .............. 250/393 |

* cited by examiner

Primary Examiner—Maureen M. Wallenhorst
(74) Attorney, Agent, or Firm—James J. McGroary; Ross F. Hunt, Jr.

(57) ABSTRACT

A dual purpose corrosion inhibitor and penetrant composition sensitive to radiography interrogation is provided. The corrosion inhibitor mitigates or eliminates corrosion on the surface of a substrate upon which the corrosion inhibitor is applied. In addition, the corrosion inhibitor provides for the attenuation of a signal used during radiography interrogation thereby providing for detection of anomalies on the surface of the substrate.

7 Claims, 1 Drawing Sheet

DUAL USE CORROSION INHIBITOR AND PENETRANT FOR ANOMALY DETECTION IN NEUTRON/X RADIOGRAPHY

STATEMENT REGARDING FEDERALLY SPONSORED RESEARCH

This invention described herein was made in the performance of work under a NASA contract and is subject to the provisions of Section 305 of the National Aeronautics and Space Act of 1958, Public Law 85-568 (72 Stat. 435, 42 U.S.C. 2457).

BACKGROUND OF THE INVENTION

1. Field of the Invention

The present invention relates to corrosion inhibition and anomaly detection and, in particular, to a corrosion inhibitor which is sensitive to either neutron radiography interrogation or X-ray interrogation, and acts as a penetrant for anomaly detection.

2. Background of the Invention

Liquid/Vapor Phase Corrosion Inhibitors (LVCI) are used to mitigate or eliminate corrosion on or in non-ferrous aluminum alloys and ferrous alloy metallic structures. Such metallic structures are employed in numerous devices such as in thrust vector control (TVC) frames as part of the Space Shuttle Vehicle (SSV), solid rocket booster (SRB) system. Typically, a paint coating is applied to the surface of TVC frames.

It is advantageous to detect anomalies in the metallic structure such as anomalies due to corrosion or cracks in the metallic surface and/or joint or weld regions. Corrosion to the TVC frame may occur over multiple SRB flight use, exposure to salt air and seawater intrusion during SRB splashdown at sea, and during towback to port for refurbishment. As a result, many TVC frames have been removed from flight use because of corrosion and other surface conditions.

The conventional method to detect corrosion internal to an aluminum alloy TVC frame is through visual inspection and may include the use of a flexible borescope. Anomalous conditions such as cracks or corrosion in a substrate under a previously painted surface will not be observed. Therefore, in many cases, the extent of corrosion and anomalous welds may not be fully determined.

One problem with manual, visual inspection, including borescopic and line-of-sight inspection, is that it is extremely labor intensive. An additional problem with visual inspection is that visual inspection cannot detect corrosion and/or cracks and anomalies under the surface of previously existing coatings such as paint. In order to effectively detect the presence of an anomaly in the substrate under the painted surface, first the paint must be removed. In the case of substrates where a previously painted surface cannot effectively be removed, visual inspection is ineffective in detecting anomalies such as cracks and corrosion present in the substrate under the painted surface. A further disadvantage with borescopic inspection is that it has limited capabilities in evaluating corner areas and areas of severe bends in a metallic structure.

Due to the limitations of visual inspection, further methods have been developed specifically for detecting cracks in the metallic structure which include ultrasonic inspection and dye penetrant detection processes. While both are effective in detecting cracks, neither of these alternative detection processes are effective in detecting corrosion damage.

The anomaly detection systems developed thus far generally fail to determine the extent of corrosion or anomalous weld conditions on the surface of a substrate. Further, these previous detection methods fail to detect corrosion under a coating of paint and in structural weld regions and, in general, cannot be used to accurately inspect corner areas, interferences, and around sharp bends. In addition, the previous detection methods tend to be labor intensive, time consuming, and tedious for the inspector.

BRIEF SUMMARY OF THE INVENTION

In accordance with the present invention, a dual use corrosion inhibitor and neutron ray or X-ray penetrant material allows for the rapid and accurate detection of an anomalous condition by the detection of corrosion by-products and active corrosion while also providing for the detection of discrepant welds and structural and adhesive bonded metal composite failures using a neutron ray process or X-ray process. The corrosion inhibitor acts as a penetrant material for detecting the anomalous condition during neutron radiography (N-ray) or X-ray interrogation. Specifically, the corrosion inhibitor absorbs (i.e., provides attenuation of) a N-ray or X-ray beam. Anomaly detection is provided by first applying the corrosion inhibitor sensitive to radiography interrogation on the surface of a substrate, followed by radiography interrogation. Anomalous conditions such as cracks and corrosion will appear visibly due to the attenuation of the neutron ray or X-ray beam used during radiography interrogation.

According to one aspect of the present invention, a composition is provided for application upon the surface of a substrate. The composition comprises a corrosion inhibitor sensitive to one of neutron radiography interrogation and X-ray interrogation. The corrosion inhibitor acts as a penetrant for anomaly detection on the surface of the substrate.

According to another aspect of the present invention, a system is provided for corrosion inhibition and anomaly detection. The system includes a substrate and a corrosion inhibitor applied to the substrate. The corrosion inhibitor is sensitive to either neutron radiography interrogation or X-ray interrogation and acts as a penetrate for anomaly detection on the substrate.

According to yet another aspect of the present invention, a method is provided for inhibiting corrosion and detecting an anomalous surface condition of a substrate. The method includes the steps of applying a corrosion inhibitor sensitive to either neutron radiography interrogation or X-ray interrogation and in which the corrosion inhibitor acts as a penetrant of the substrate. An anomaly is detected on the substrate using either neutron radiography or X-ray radiography.

A key feature of the present invention is a dual use material which provides both protection of a substrate by mitigating or eliminating active corrosion as well as serving as a penetrant sensitive to radiography interrogation. As a result, significant time is saved from not having to use two processes independently, namely a corrosion inhibitor process and a radiography penetrant material application process. Consequently, an advantage of the dual use material is the associated decrease in costs associated with the reduction in processing steps.

An additional feature of the present invention relates to a corrosion inhibitor sensitive to radiography interrogation which provides for the detection of currently present anomalous conditions such as cracks and corrosion, as well as for detection of future, latent structural defects or anomalies which occur in the substrate at some future point after the application of the corrosion inhibitor. For example, the present corrosion inhibitor provides for detection of anomalous conditions immediately after the application of the corrosion inhibitor to detect any initial anomalous conditions. In addition, the same substrate may be monitored for corrosion or other anomalous conditions after the substrate has been used by reexamining the substrate with radiography interrogation after the substrate has been subjected to various operating conditions and stresses.

Yet another feature of the present invention relates to the detection of anomalous surface conditions of a substrate present underneath a painted surface. The corrosion inhibitor sensitive to radiography interrogation is first applied to the surface of the substrate prior to applying a paint coating over the corrosion inhibitor. After subsequent use, the substrate can be monitored for anomalous conditions by radiography interrogation through the painted substrate surface.

One advantage of detecting an anomalous condition under a painted surface is the elimination of the need to remove the paint in order to detect the anomalous condition. Further, the present detection system provides for detecting anomalous conditions in areas where the removal of paint is difficult or impossible.

Additional features and advantages of the present invention will be set forth in, or apparent from, the detailed description of preferred embodiments thereof which follows,

DETAILED DESCRIPTION OF THE INVENTION

Figure 1:
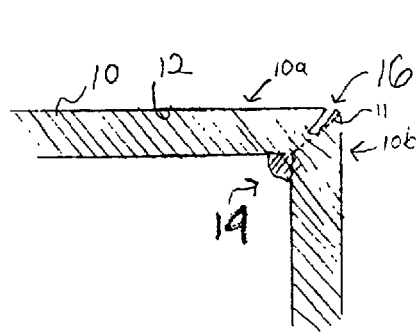
FIG. 1 is a schematic neutron radiograph of a substrate without a corrosion inhibitor sensitive to radiography interrogation according to the present invention.

Referring now to FIG. 1, depicted therein is a schematic neutron radiograph showing a baseline view of a substrate 10 prior to the application of a corrosion inhibitor. Substrate 10 includes substrate portions 10a, 10b with mitered ends (indicated by broken line 11) joined together at weld 14. Substrate 10 may include materials such as non-ferrous metals and alloys including alloys of aluminum, magnesium, copper, zinc, beryllium, or ferrous alloys. In addition, substrate 10 may include composite structures composed of organic/metallic materials. As an example, weld 14 includes a crack 16. In an actual radiograph, the crack 16 will appear indistinguishable from the background and therefore, crack 16 will be difficult to observe.

Figure 2A:
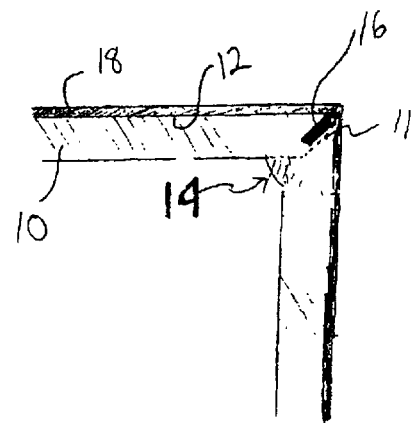
FIG. 2(a) is a schematic of the substrate of FIG. 1 after the application of the corrosion inhibitor sensitive to radiograph interrogation.
Figure 2B:
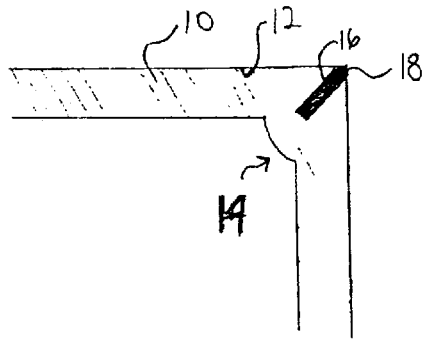
FIG. 2(b) is a schematic neutron radiograph of the substrate of FIG. 2(a)

Referring now to FIGS. 2(a) and 2(b), corrosion inhibitor 18 is applied to the surface 12 of the substrate 10. The corrosion inhibitor 18 mitigates and/or eliminates corrosion on or in non-ferrous alloys and ferrous metallic materials. As discussed above, corrosion inhibitor 18 also mitigates and/or eliminates corrosion in composite/metallic combinations. If the substrate 10 is to be subjected to various stress conditions such as heat and salt water, optimally the corrosion inhibitor 18 is a liquid/vapor phase corrosion inhibitor (LVCI). Alternatively, the corrosion inhibitor can be other liquid polymer forms that also may be part of a composite resin system with built in corrosion inhibitors, tracers, and/or dopants.

Corrosion inhibitor 18 is also sensitive to neutron radiography interrogation and serves as a penetrant. The viscosity of corrosion inhibitor is adjusted as necessary to provide the desired penetration properties. As such, corrosion inhibitor 18 penetrates (i.e., fills in) the crack 16.

Referring now specifically to the neutron radiograph of FIG. 2(b), crack 16 becomes highly visible due to the presence of the corrosion inhibitor 18 present in crack 16 as compared with the non filled-in crack 16 depicted in FIG. 1. Specifically, anomalous conditions, such as crack 16, appears highly visibly due to the attenuation of the neutron ray beam used during radiography interrogation.

The neutron radiography proess includes adjusting both the length of film exposure and development time to provide a maximum contrast for any surface anomaly now filled with the corrosion inhibitor 18. The corrosion inhibitor disposed along the substrate surface 12 not visible In the neutron radiograph due to the optimal exposure settings used to maximize the detection of surface anomalies such as the crack 16.

The detection of anomalies such as the crack 16 may be enhanced further by utilizing various additives such as dopants to the corrosion inhibitor 18 to provide acceptable neutron-ray attenuation in the desired area. As a result, any anomaly present will become more visible even if the anomaly is off-plane from the neutron-ray beam. Thus, the addition of a dopant provides for maximum anomaly detection. Further, a wide variety of corrosion inhibitors can be modified, via dopant addition, to make the various corrosion inhibitors sensitive to a desired radiography interrogation process.

Figure 3A:
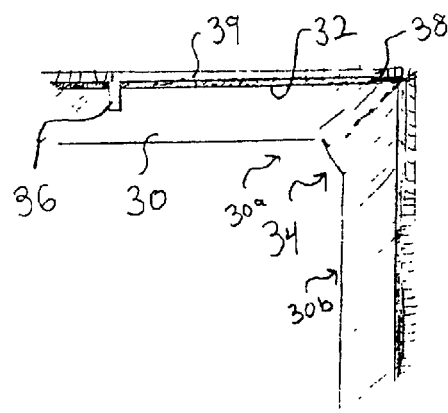
FIG. 3(a) is a schematic of a substrate with an anomalous surface condition occurring in the substrate subsequent to use.

Referring now to FIG. 3(a), substrate 30 includes a substrate surface 32 upon which corrosion inhibitor 38 and a coating of paint 39 are applied. A weld 34 joins the mitered ends of substrate portions 30a and substrate portion 30b. Anomaly 36 was formed on surface 3 under the previously applied coating of paint 39 due to corrosion of the material comprising substrate 30. Since anomaly 36 is disposed under the coating of paint 39, the anomaly 36 is not observable via visual inspection.

Figure 3B:
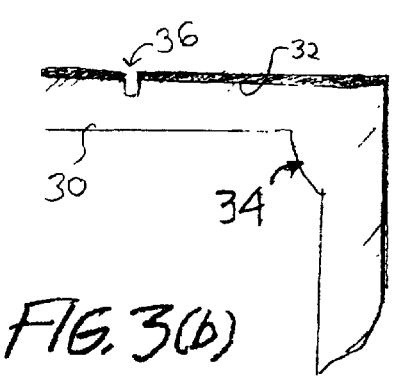
FIG. 3(b) is a schematic radiograph of the substrate of FIG. 3(a).

Referring now to FIG. 3(b), depicted is a neutron radiograph of the substrate 30. The anomaly 36 is detected on the radiograph as a gap in the corrosion inhibitor layer 38 as a result of the erosion of, i.e., the removal of, a portion of the substrate 30. The length of exposure and development time of the film are optimized to provide the maximum contrast for the corrosion inhibitor layer 38 thereby making the anomaly 36 most readily discernable as a gap in the corrosion inhibitor layer 38. As a result, although the anomaly 36 is located underneath the coating of paint 39, the anomaly 36 is detectable by neutron radiography interrogation.

What will now apparent to one of ordinary skill in the art is that the present invention may be extended to numerous substrate materials and appropriate corrosion inhibitors sensitive to various radiography interrogation techniques. For example, numerous applications exist for the present invention in corrosion protection of aircraft, boats, trains, automobiles, and building structures. The inspection of these structures can be enhanced through the use of the LVCI/penetrant inspection material.

While neutron radiography interrogation is described herein, the present invention may be modified for use with X-ray interrogation whereby the corrosion inhibitor is sensitive to X-ray. Further, the corrosion inhibitor may be doped with material which provides further X-ray attenuation.

Alternatively, laser ultrasonics, holography and other non-destructive examination techniques can be used to detect anomalies using an appropriate combination corrosion inhibitor with a respective detector material. As with neutron radiography and X-ray interrogation, the respective detector material amplifies the respective signal of the nondestructive examination technique to assist in locating and identifying anomalous conditions. For example, the respective detector material could be a dopant which amplifies acoustic signals for detection using laser ultrasonics or a material which enhances a thermal energy response during holography.

Although the invention has been described above in relation to preferred embodiments thereof, it should be obvious by those skilled in the art that variations and modifications can be effectuated in these preferred embodiments without departing from the scope and spirit of the invention.

What is claimed is:

1. A method for inhibiting corrosion and for detecting cracks and other anomalous surface conditions of a metallic substrate forming part of a flight structure, said method comprising the steps of:

applying a liquid/vapor chase corrosion inhibitor to a surface of the metallic substrate forming part of a flight structure, said corrosion inhibitor being sensitive to one of neutron radiography interrogation and X-ray interrogation and, when applied, penetrating into the substrate; and detecting crack or other anomaly on or in the metallic substrate using one of neutron radiography and X-ray radiography.

2. The method of claim 1, wherein said anomaly comprises a corrosion anomaly in the substrate.

3. The method of claim 2, wherein the step of detecting an anomaly comprises detecting corrosion by-products.

4. The method of claim 2, wherein the step of detecting an anomaly comprises detecting active corrosion.

5. The method of claim 1, wherein the substrate comprises a weld region in the flight structure and the step of detecting an anomaly comprises detecting an anomaly in the weld region.

6. The method of claim 1, further comprising:

applying a coating layer over the corrosion inhibitor; and wherein the step of detecting an anomaly comprises detecting an anomaly located on the under the coating layer.

7. The method of claim 1, wherein the step of detecting an anomaly comprises irradiating the substrate with a neutron ray off-plane from a plane of the substrate.

* * * * *